United States Patent
Kobayashi et al.

(10) Patent No.: US 11,421,102 B2
(45) Date of Patent: Aug. 23, 2022

(54) METHOD FOR MANUFACTURING POROUS PARTICLES, POROUS PARTICLES, CARRIER, COLUMN, AND METHOD FOR SEPARATING TARGET SUBSTANCE

(71) Applicants: JSR CORPORATION, Minato-ku (JP); JSR LIFE SCIENCES, LLC, Sunnyvale, CA (US); JSR MICRO N.V., Leuven (BE)

(72) Inventors: Kunihiko Kobayashi, Minato-ku (JP); Masaaki Kanahara, Minato-ku (JP)

(73) Assignees: JSR CORPORATION, Minato-ku (JP); JSR LIFE SCIENCES, LLC, Sunnyvale, CA (US); JSR MICRO N.V., Leuven (BE)

( * ) Notice: Subject to any disclaimer, the term of this patent is extended or adjusted under 35 U.S.C. 154(b) by 108 days.

(21) Appl. No.: 15/778,436

(22) PCT Filed: Nov. 24, 2016

(86) PCT No.: PCT/JP2016/084743
§ 371 (c)(1),
(2) Date: May 23, 2018

(87) PCT Pub. No.: WO2017/090658
PCT Pub. Date: Jun. 1, 2017

(65) Prior Publication Data
US 2018/0346704 A1    Dec. 6, 2018

(30) Foreign Application Priority Data
Nov. 24, 2015 (JP) .............................. JP2015-229126

(51) Int. Cl.
| | |
|---|---|
| C08L 29/04 | (2006.01) |
| C08J 9/28 | (2006.01) |
| C08J 3/16 | (2006.01) |
| G01N 30/88 | (2006.01) |
| B01J 20/32 | (2006.01) |
| B01J 20/28 | (2006.01) |
| B01J 20/26 | (2006.01) |
| B01J 20/286 | (2006.01) |
| B01D 15/38 | (2006.01) |
| C07K 16/18 | (2006.01) |
| C08F 210/02 | (2006.01) |
| C08F 216/06 | (2006.01) |

(52) U.S. Cl.
CPC .......... *C08L 29/04* (2013.01); *B01D 15/3804* (2013.01); *B01D 15/3809* (2013.01); *B01J 20/261* (2013.01); *B01J 20/264* (2013.01); *B01J 20/265* (2013.01); *B01J 20/267* (2013.01); *B01J 20/286* (2013.01); *B01J 20/28054* (2013.01); *B01J 20/321* (2013.01); *B01J 20/3274* (2013.01); *C08J 3/16* (2013.01); *C08J 9/28* (2013.01); *G01N 30/88* (2013.01); *B01D 2257/70* (2013.01); *C07K 16/18* (2013.01); *C08F 210/02* (2013.01); *C08F 216/06* (2013.01); *C08L 2203/02* (2013.01); *C08L 2312/00* (2013.01)

(58) Field of Classification Search
CPC .... C08F 216/06; C08L 29/04; C08L 2312/00; B01J 20/267; B01D 15/3804
See application file for complete search history.

(56) References Cited

U.S. PATENT DOCUMENTS

| | | | |
|---|---|---|---|
| 4,863,972 A * | 9/1989 | Itagaki | ................... B01D 15/34 521/141 |
| 5,811,488 A | 9/1998 | Narumoto et al. | |
| 6,204,033 B1 | 3/2001 | Muller-Schulte | |
| 2001/0014468 A1 * | 8/2001 | Muller-Schulte | ...... C07K 16/26 435/181 |
| 2003/0185895 A1 | 10/2003 | Lanphere et al. | |
| 2005/0249896 A1 | 11/2005 | Chen et al. | |

FOREIGN PATENT DOCUMENTS

| | | | |
|---|---|---|---|
| CA | 2356857 A1 * | 7/2000 | ................ B01L 3/50 |
| CN | 1671782 A | 9/2005 | |
| DE | 3900945 A1 | 7/1990 | |
| EP | 0 256 293 A2 | 2/1988 | |

(Continued)

OTHER PUBLICATIONS

Barrett et al. "Resistance to Nonspecific Protein Adsorption by Poly(vinyl alcohol) Thin Films Adsorbed to a Poly(styrene) Support Matrix Studied Using Surface Plasmon Resonance" (Analytical Chemistry, 73, 2001, p. 5232-5239). (Year: 2001).*
Wang et al. "Novel in situ crosslinking reaction of ethylene-vinyl alcohol copolymers by propylene carbonate" (Materials Letters 60, 2006, 509-513). (Year: 2006).*
Rudra et al. "Acid catalysed cross-linking of poly vinyl alcohol (PVA) by glutaraldehyde: effect of crosslink density on the characteristics of PVA membranes used in single chambered microbial fuel cells" (RSC Adv., 5; 2015, p. 83436-83447). (Year: 2015).*
Extended European Search Report dated May 23, 2019, in Patent Application No. 16868601.2, 11 pages.

(Continued)

*Primary Examiner* — Ryan B Huang
(74) *Attorney, Agent, or Firm* — Oblon, McClelland, Maier & Neustadt, L.L.P.

(57) ABSTRACT

To provide a porous particle with which non-specific adsorption is hardly generated although the porous particle is a synthetic polymer-based particle, the mechanical strength is high, and the dynamic binding capacity is high in a case where a ligand is bound to the porous particle; and a method for producing the same. A method for producing a porous particle, including the following steps 1 and 2; (step 1) dissolving at least one or more of polymers selected from the group consisting of a vinyl alcohol polymer and an ethylene-vinyl alcohol copolymer in an aqueous solvent to prepare a polymer solution; and (step 2) dispersing the polymer solution in a non-aqueous solvent to form a W/O emulsion.

8 Claims, 1 Drawing Sheet

(56) References Cited

FOREIGN PATENT DOCUMENTS

| | | | |
|---|---|---|---|
| JP | 2-8230 A | | 1/1990 |
| JP | 2-8230 A | * | 1/1990 |
| JP | 02008230 A | * | 1/1990 |
| JP | 2-55714 A | | 2/1990 |
| JP | 05132859 A | * | 5/1993 |
| JP | 9-316272 A | | 12/1997 |
| JP | 11-510836 A | | 9/1999 |
| JP | 2005-325352 A | | 11/2005 |
| JP | 2005-535752 A | | 11/2005 |
| JP | 2010-233825 A | | 10/2010 |
| JP | 2011-224360 A | | 11/2011 |
| JP | 2012-214550 A | | 11/2012 |
| WO | WO98/04616 A1 | | 2/1998 |

OTHER PUBLICATIONS

International Search Report dated Feb. 28, 2017 in PCT/JP2016/084743 filed Nov. 24, 2016.
Combined Taiwanese Office Action and Search Report dated Apr. 30, 2020 in Patent Application No. 105138685 (with unedited computer generated English translation), 12 pages.

* cited by examiner

METHOD FOR MANUFACTURING POROUS PARTICLES, POROUS PARTICLES, CARRIER, COLUMN, AND METHOD FOR SEPARATING TARGET SUBSTANCE

TECHNICAL FIELD

The present invention relates to a method for producing a porous particle, a porous particle, a carrier, a column, and a method for separating a target substance.

BACKGROUND ART

It is difficult to separate a target substance such as a protein or an antibody from a biological sample such as serum, blood plasma, a cell culture solution, or urine, and thus a technique for efficiently separating the target substance has been required.

For example, for the purpose of selectively separating a target substance from a biological sample, a carrier in which an organic porous particle constituted of a synthetic polymer is used as a support and a ligand is bound to the support, has been used.

As the carrier using an organic porous particle constituted of a synthetic polymer as a support, a carrier using, for example, polyacrylamide gel, polyacrylate gel, polystyrene, or an ethylene-vinyl alcohol copolymer has been developed (Patent Literatures 1 and 2). Meanwhile, a synthetic polymer-based porous particle has a disadvantage that non-specific adsorption easily occurs.

CITATION LIST

Patent Literature

Patent Literature 1: JP 2011-224360 A
Patent Literature 2: JP 2012-214550 A

SUMMARY OF INVENTION

Technical Problem

In particular, it is not easy to satisfy the dynamic binding capacity in a case where a ligand is bound while suppressing non-specific adsorption, and in addition to this, it has been considered to be particularly difficult to have sufficient mechanical strength.

The problem to be solved by the present invention is to provide a porous particle with which non-specific adsorption is hardly generated despite a synthetic polymer-based particle, the mechanical strength is high, and the dynamic binding capacity is high in a case where a ligand is bound to the porous particle, and a method for producing the porous particle.

Solution to Problem

Accordingly, the inventors of the present invention conducted a thorough investigation, and as a result, it found that with the production by a method including (step 1) a step of dissolving at least one or more of polymers selected from the group consisting of a vinyl alcohol polymer and an ethylene-vinyl alcohol copolymer in an aqueous solvent to prepare a polymer solution, and (step 2) a step of dispersing the polymer solution in a non-aqueous solvent to form a W/O emulsion, a porous particle with which non-specific adsorption is hardly generated despite a synthetic polymer-based particle, the mechanical strength is high, and the dynamic binding capacity is high in a case where a ligand is bound to the porous particle is obtained. Thus, they have completed the present invention.

Further, the present inventors found by a porous particle derived from one or more of polymers selected from the group consisting of a vinyl alcohol polymer and an ethylene-vinyl alcohol copolymer, and having a void ratio of 75% or more, non-specific adsorption is hardly generated despite a synthetic polymer-based particle, the mechanical strength is high, and the dynamic binding capacity is high in a case where a ligand is bound to the porous particle. Thus, they have completed the present invention.

That is, the present invention is to provide the following [1] to [15].

[1] A method for producing a porous particle, including the following steps 1 and 2 (hereinafter, also referred to as a "method for producing a porous particle of the present invention"):

(step 1) dissolving at least one or more of polymers selected from the group consisting of a vinyl alcohol polymer and an ethylene-vinyl alcohol copolymer in an aqueous solvent to prepare a polymer solution; and (step 2) dispersing the polymer solution in a non-aqueous solvent to form a W/O emulsion.

[2] The method for producing a porous particle according to [1], wherein as the ethylene-vinyl alcohol copolymer, an ethylene-vinyl alcohol copolymer having a repeating unit (hereinafter, also referred to as a "repeating unit (1)") derived from ethylene represented by Formula (1) in an amount exceeding 0% by mole and 50% by mole or less relative to an entire repeating unit in the copolymer is used.

[3] The method for producing a porous particle according to [1] or [2], further including the following step 3:

(step 3) cooling the W/O emulsion to form a porous particle.

[4] The method for producing a porous particle according to [3], further including the following step 4:

(step 4) chemically crosslinking the porous particle formed in step 3.

[5] The method for producing a porous particle according to any one of [1] to [4], wherein the aqueous solvent is a mixed solvent containing one or more selected from the group consisting of a solvent miscible with water among sulfoxide-based solvents, a solvent miscible with water among polyol-based solvents, a solvent miscible with water among alcohol-based solvents, and a solvent miscible with water among amide-based solvents, and water; or water.

[6] A porous particle derived from one or more of polymers selected from the group consisting of a vinyl alcohol polymer and an ethylene-vinyl alcohol copolymer, wherein the porous particle has a void ratio of 75%- or more (hereinafter, also referred to as a "porous particle of the present invention").

[7] The porous particle described in [6], in which the ethylene-vinyl alcohol copolymer is an ethylene-vinyl alcohol copolymer having a repeating unit (1) in an amount exceeding 0% by mole and 50% by mole or less relative to an entire repeating unit in the copolymer.

[8] The porous particle according to [6] or [7], which has a chemically cross-linked structure.

[9] The porous particle according to any one of [6] to [8], which has a repeating unit (hereinafter, also referred to as a "repeating unit (2)") derived from vinyl alcohol represented by Formula (2).

[10] A carrier (hereinafter, also referred to as a "carrier of the present invention"), comprising the porous particle according to any one of [6] to [9] having a ligand bound thereto.

[11] The carrier according to [10], wherein the ligand is a protein containing an immunoglobulin binding domain.

[12] The carrier according to [10] or [11], which is used for separation of a target substance.

[13] The carrier according to [10] or [11], which is used for adsorbing body fluid perfusion.

[14] A column (hereinafter, also referred to as a "column of the present invention"), comprising a column container having the carrier according to any one of [10] to [13] packed therein.

[15] A method for separating a target substance (hereinafter, also referred to as a "method for separating a target substance of the present invention"), comprising using the carrier according to any one of [10] to [13].

Advantageous Effects of Invention

According to the method for producing a porous particle of the present invention, a porous particle with which non-specific adsorption is hardly generated although the porous particle is a synthetic polymer-based particle, the mechanical strength is high, and the dynamic binding capacity is high in a case where a ligand is bound to the porous particle, can be simply and easily produced.

The porous particle of the present invention, with which non-specific adsorption is hardly generated although the porous particle is a synthetic polymer-based particle, the mechanical strength is high, and the dynamic binding capacity is high in a case where a ligand is bound to the porous particle.

DESCRIPTION OF EMBODIMENTS

[Porous Particle]

The porous particle of the present invention is a porous particle derived from one or more of polymers selected from the group consisting of a vinyl alcohol polymer and an ethylene-vinyl alcohol, and has a void ratio of 75% or more.

(Void Ratio)

The void ratio of the porous particle of the present invention is 75% or more. By setting the void ratio to 75% or more, the dynamic binding capacity in a case where a ligand is bound can be dramatically increased.

The void ratio is, from the viewpoint of the dynamic binding capacity and the target substance capturing performance in a case where a ligand is bound, preferably 80% or more, more preferably 85% or more, and particularly preferably 90% or more; and further is, from the viewpoint of the mechanical strength, preferably less than 100%, and more preferably 95% or less. In particular, by setting the void ratio to 80% or more, the dynamic binding capacity is significantly improved in a case where a ligand is bound.

The void ratio can be calculated by packing a column container with porous particles, and passing a standard substance through the column container. Specifically, the void ratio may be measured in a similar manner as in Examples.

As the porous particle of the present invention, from the viewpoint of the mechanical strength or the dynamic binding capacity in a case where a ligand is bound, a porous particle having a crystal structure is preferred. The presence or absence of the crystal structure can be confirmed by, for example, an X-ray diffraction. Further, in the present specification, the porous particle means a particle having a large number of pores on the surface of the particle.

Herein, the vinyl alcohol polymer and the ethylene-vinyl alcohol copolymer used in the present invention will be described in detail.

The above vinyl alcohol polymer means a polymer constituted of a repeating unit derived from vinyl alcohol represented by the following Formula (2).

Further, the above ethylene-vinyl alcohol copolymer means a polymer constituted of a repeating unit derived from ethylene represented by the following Formula (1) and a repeating unit (2). In addition, the ethylene-vinyl alcohol copolymer may be any copolymer of, for example, a random copolymer, a block copolymer, and a graft copolymer, or a mixture thereof.

In the ethylene-vinyl alcohol copolymer used in the present invention, the content of the repeating unit (1) is exceeding 0% by mole relative to an entire repeating unit in the ethylene-vinyl alcohol copolymer, and is, from the viewpoint of the dynamic binding capacity in a case where a ligand is bound, preferably exceeding 1% by mole, more preferably exceeding 5% by mole, furthermore preferably 10% by mole or more, and particularly preferably 15% by mole or more, relative to an entire repeating unit in the ethylene-vinyl alcohol copolymer; and further is, from the viewpoint of the amount of non-specific adsorption, the exclusion limit molecular weight, or the dynamic binding capacity in a case where a ligand is bound, preferably 50% by mole or less, more preferably 45% by mole or less, furthermore preferably 40% by mole or less, still furthermore preferably 35% by mole or less, and particularly preferably 30% by mole or less.

In addition, the ethylene-vinyl alcohol copolymer has a repeating unit (2) in addition to the repeating unit (1), and the content of the repeating unit (2) is the balance other than the repeating unit (1).

The content of the repeating units (1) and (2) can be calculated, for example, by NMR measurement of the ethylene-vinyl alcohol copolymer.

(Saponification Degree)

The saponification degree of the vinyl alcohol polymer and the ethylene-vinyl alcohol copolymer used in the present invention is, from the viewpoint of the amount of non-specific adsorption, preferably 90% by mole or more, more preferably 92% by mole or more, furthermore preferably 95% by mole or more, and particularly preferably 98% by mole or more. Further, the upper limit may be 100% by mole or less, and preferably 99.9% by mole or less.

In the present specification, the saponification degree can be measured in accordance with JIS K6726.

(Polymerization Degree)

The polymerization degree of the vinyl alcohol polymer and the ethylene-vinyl alcohol copolymer used in the present invention 0 the viewpoint of the mechanical strength, preferably 50 or more, and more preferably 100 or more; and further is, from the point that the viscosity of the solution can be suppressed and the granulation becomes easy in the case where a polymer solution prepared by dissolving the vinyl alcohol polymer and the ethylene-vinyl alcohol copolymer in an aqueous solvent, preferably less than 1000, and more preferably less than 500.

In the present specification, the polymerization degree means a viscosity-average polymerization degree, and can be calculated in accordance with JIS K6726.

As the raw material for the porous particle of the present invention, in addition to a vinyl alcohol polymer, and an ethylene-vinyl alcohol copolymer, other polymers (for example, polyvinyl pyrrolidone) or the monomers thereof may be used in combination. The content of the polymer part derived from one or more of the polymers selected from the group consisting of a vinyl alcohol polymer and an ethylene-vinyl alcohol copolymer is preferably 85 to 100% by mass, more preferably 90 to 100% by mass, furthermore preferably 95 to 100% by mass, and particularly preferably 99 to 100% by mass, relative to an entire repeating unit contained in the porous particle.

As the raw material polymer for a porous particle, for example, from the point of easily forming the crystal structure and improving the mechanical strength, from the point of obtaining the exclusion limit molecular weight at which a porous particle becomes suitable for the use in a carrier after a ligand is bound, and from the point of improving the dynamic binding capacity and the target substance capturing performance in a case where a ligand is bound, a raw material polymer constituted of the repeating units (1) and (2), that is, an ethylene-vinyl alcohol copolymer is particularly preferred.

The vinyl alcohol polymer, and the ethylene-vinyl alcohol copolymer may be a product available on the market, or a product synthesized according to a conventional method. The vinyl alcohol polymer and the ethylene-vinyl alcohol copolymer are produced, in general, by polymerizing a vinyl acetate monomer, or copolymerizing a vinyl acetate monomer and ethylene, and then by saponifying the resultant material.

(Chemically Cross-Linked Structure)

As the porous particle of the present invention, a porous particle having a chemically cross-linked structure is preferred. According to this, the mechanical strength, and the pressure resistance are improved, and the porous particle can be used at a higher flow rate, for example, in a case of being used after a ligand is bound.

As the chemically cross-linked structure, a crosslinking structure in which a residue of the hydroxy group in two or more repeating units (2) contained in a porous particle is chemically crosslinked is preferred, and a crosslinking structure in which a residue of the hydroxy group in two or more repeating units (2) contained in a porous particle is chemically crosslinked with a single bond or a divalent or higher-valent linking group is more preferred. In this case, the porous particle may contain both a repeating unit (2) and a structure in which a repeating unit (2) is chemically cross-linked (among the repeating units (2) contained in a porous particle, some of the repeating units (2) may be chemically crosslinked or all of the repeating units (2) may be chemically crosslinked).

As the above single bond or divalent or higher-valent linking group, one derived from a crosslinking agent can be mentioned. Further, as the divalent or higher-valent linking group, a divalent to tetravalent linking group is preferred, and from the viewpoint of, for example, the mechanical strength, a tetravalent linking group is particularly preferred.

Examples of the crosslinking agent include an aldehyde compound, an epoxy compound, a N-methylol compound, a dicarboxylic acid, a halogen compound, and an isocyanate compound, an aldehyde compound, an epoxy compound, and a N-methylol compound are preferred, and from the point of the easy reaction control, an aldehyde compound is preferred.

Specific examples of the aldehyde compound include a monoaldehyde compound such as formaldehyde, acetaldehyde, propionaldehyde, crotonaldehyde, and benzaldehyde; a dialdehyde compound such as glyoxal, malondialdehyde, succinaldehyde, adipaldehyde, citraldehyde, phthalaldehyde, isophthalaldehyde, malealdehyde, glutaraldehyde, and terephthalaldehyde, and a polyaldehyde compound such as dialdehyde starch, and polyacrolein. Among them, from the viewpoint of the mechanical strength, a dialdehyde compound is preferred, and from the point of the high safety, glutaraldehyde is particularly preferred.

Specific examples of the epoxy compound include bifunctional bisepoxides such as ethylene glycol diglycidyl ether, neopentyl glycol diglycidyl ether, resorcinol diglycidyl ether, hydrogenated bisphenol A diglycidyl ether, glycerol diglycidyl ether, trimethylolpropane diglycidyl ether, diethylene glycol diglycidyl ether, and propylene glycol diglycidyl ether; tri- or more-functional polyepoxides such as glycerol polyglycidyl ether, trimethylolpropane polyglycidyl ether, pentaerythritol polyglycidyl ether, diglycerol polyglycidyl ether, polyglycerol polyglycidyl ether, and sorbitol polyglycidyl ether; epihalohydrins such as epichlorohydrin, epibromohydrin, epifluorohydrin, and epiiodohydrin; and glycidol.

Specific examples of the N-methylol compound include dimethylol urea, dimethylol ethylene urea, dimethylol propylene urea, dimethylol uron, dimethylol triazone, dimethylol-4-methoxy-5,5-dimethylpropyleneurea, dimethylol dihydroxy ethylene urea, dimethylol alkyl carbamate, methylated dimethylol dimethoxyethylene urea, 1,3-dimethyl-4,5-dihydroxy ethylene urea, trimethylol melamine, hexamethylol melamine, methylated trimethylol melamine, and methylated hexamethylol melamine.

(Reactive Functional Group)

As the porous particle of the present invention, a porous particle having a reactive functional group capable of binding to a ligand is preferred. The porous particle in such an embodiment can be used as a carrier only by binding a ligand and is useful as a support.

As the reactive functional group capable of binding to a ligand, a carboxyl group, a formyl group, an amino group, a maleimide group, an active ester group, or an epoxy group is preferred. Among them, from the point that the reaction with a ligand proceeds under mild conditions, an epoxy group is particularly preferred.

(Distribution Coefficient Kav, And Exclusion Limit Molecular Weight)

The Kav of the porous particle of the present invention is, from the viewpoint of the dynamic binding capacity in a case where a ligand is bound, preferably 0.2 or more, more preferably 0.4 or more, furthermore preferably 0.5 or more, and particularly preferably 0.6 or more; and further is, from the viewpoint of the amount of non-specific adsorption, or the dynamic binding capacity in a case where a ligand is bound, preferably 0.9 or less, more preferably 0.8 or less, and particularly preferably 0.75 or less.

The exclusion limit molecular weight of the porous particle of the present invention is, from the viewpoint of the amount of non-specific adsorption or the dynamic binding capacity in a case where a ligand is bound, preferably 500 KDa or more, more preferably 1000 KDa or more, furthermore preferably 10000 KDa or more, furthermore preferably 50000 KDa or more, still furthermore preferably 75000 KDa or more, and particularly preferably 100000 KDa or more; and further is, from the viewpoint of the amount of non-specific adsorption or the target substance capturing performance in a case where a ligand is bound, preferably 1000000 KDa or less, more preferably 750000 KDa or less, and particularly preferably 500000 KDa or less.

The distribution coefficient Kav and the exclusion limit molecular weight mean a Kav and an exclusion limit molecular weight, respectively, which are calculated by packing a column container with porous particles and passing a standard substance through the column container, and specifically, may be measured in a similar manner as in Examples.

(Bulk Density)

The bulk density of the porous particles of the present invention is, from the viewpoint of, for example, the mechanical strength and the amount of bound ligands, preferably 0.005 g/mL or more, more preferably 0.01 g/mL or more, and particularly preferably 0.05 g/mL or more; and further is, from the viewpoint of the dynamic binding capacity and the target substance capturing performance in a case where a ligand is bound, preferably 1 g/mL or less, more preferably 0.5 g/mL or less, furthermore preferably 0.3 g/mL or less, and particularly preferably 0.14 g/mL or less. In particular, by setting the bulk density to 0.14 g/mL or less, the dynamic binding capacity is significantly improved in a case where a ligand is bound.

The bulk density means a weight of a packed bed of porous particles per volume, and specifically, may be measured in a similar manner as in Examples.

(Specific Surface Area)

The specific surface area of the porous particle of the present invention is, from the viewpoint of the amount of non-specific adsorption, the mechanical strength, or the dynamic binding capacity in a case where a ligand is bound, preferably 50 $m^2/g$ or more, more preferably 70 $m^2/g$ or more, furthermore preferably 80 $m^2/g$ or more, and particularly preferably 90 m/g or more; and further is, from the viewpoint of the mechanical strength, preferably 150 $m^2/g$ or less.

The specific surface area of the present invention means a value obtained by dividing the surface area of porous particles having pores with a pore diameter of 10 to 5000 nm obtained by a mercury porosimeter by the dry mass of porous particles.

(Average Particle Diameter)

The average particle diameter of the porous particles of the present invention is preferably 10 to 1000 μm. By setting the average particle diameter to 10 μm or more, the increase in back pressure is suppressed in a case where the porous particle is used for separation of a target substance after a ligand is bound, and the porous particle becomes easy to use even at a high flow rate. On the other hand, by setting the particle diameter to 1000 μm or less, for example, in separation of a target substance, even the pores inside the particle can be efficiently utilized.

The average particle diameter means a volume average particle diameter as measured by a laser diffraction method in accordance with ISO 13320 and JIS Z 8825-1. Specifically, the average particle diameter means an average particle diameter determined by measuring a particle size distribution with a laser scattering diffraction type particle size distribution measuring device (for example, LS 13 320 (manufactured by Beckman Coulter, Inc.) and by measuring a volume-based particle size distribution using, for example, Fluid R. I. Real 1.333, or Sample R.I. Real 1.54 Imaginary 0 as an optical model.

The porous particle of the present invent ion may be a porous particle into which the above-described chemically cross-linked structure or a reactive functional group has been introduced, however, even in such a case, as the porous particle, the porous particle may have a repeating unit (2).

In addition, the porous particle of the present invention is excellent in the reduction in the amount of the adsorption to, for example, impurities derived from a living body such as a host cell protein (HCP) or DNA contained in a host cell although the porous particle is a synthetic polymer-based particle, and has excellent antifouling properties. Further, the porous particle of the present invention has high mechanical strength, and high dynamic binding capacity of a target substance in a case where a ligand is bound.

[Carrier]

The carrier of the present invention is a carrier in which a ligand is bound to the porous particle of the present invention. Note that the carrier of the present invention has a granular shape. As the carrier of the present invention, from the viewpoint of the amount of non-specific adsorption, the mechanical strength, or the dynamic binding capacity, a carrier having a crystal structure is preferred. The presence or absence of the crystal structure can be confirmed by; for example, an X-ray diffraction.

In addition, the binding of the ligand to a porous particle may be a direct binding, or an indirect binding via, for example, a linker.

The carrier of the present invention can be produced according to a conventional method in which, for example, a ligand is bound to a porous particle according to a covalent binding procedure except that the porous particle of the present invention is used. As the technique for binding a ligand, a technique in which the above-described reactive functional group is used as it is as a binding site to a ligand is preferred from the point of the simple process. In addition, in a case where the reactive functional group is an epoxy group, a method in which an alcoholic hydroxyl group formed by ring-opening of an epoxy group contained in a porous particle is activated with, for example, a tosyl group, and then a ligand is bound, or a Method in which a linker is further extended from an epoxy group contained in a porous particle or a ring-opened epoxy group formed by ring-opening of the epoxy group, and then a ligand is bound via the linker can be mentioned.

The binding conditions of a ligand may be appropriately selected depending on the content of the reactive functional group or the kind of the ligand. In a case where the ligand is a protein, for example, an amino group at the N-terminal of the protein, an s-amino group of a lysine residue contained in the protein, or a mercapto group of a cysteine residue can become a reaction point with a reactive functional group such as an epoxy group. In a case where the protein is bound, for example, by using an aqueous solution of buffers having an isoelectric point close to that of the protein, adding a salt such as sodium chloride, or sodium sulfate to the solution, as needed, and allowing the protein and the porous particles to react with each other at 0 to 40° C. for 1 to 48 hours while mixing the protein and the porous particles in the solution, the protein can be bound to a reactive functional group.

In addition, after the ligand is bound, the reactive functional groups remaining in the carrier may be subjected to a hydrophilization treatment (blocking treatment). The treatment to the reactive functional groups may be performed according to a known method, and as the specific technique, a technique in which an alcohol containing a mercapto group, such as mercaptoethanol, or thioglycerol is reacted with reactive functional groups remaining in a carrier can be mentioned.

(Ligand)

As the ligand binding to the porous particle of the present invention, the kind of the ligand is not particularly limited as long as the ligand has a moderate affinity for a target substance. As a specific example of the ligand, a low molecular compound of a protein such as protein A, protein G, protein L, Fc-binding protein, avidin, streptavidin, lectin, or a functional variant thereof; amino acid; a peptide such as insulin; an antibody such as a monoclonal antibody; antigen; enzyme; hormone; a nucleic acid such as DNA, or RNA; nucleotide; nucleoside; a sugar or polysaccharide such as heparin, Lewis X, or ganglioside; iminodiacetic acid, synthetic dye, 2-aminophenylboronic acid, 4-aminobenzamidine, glutathione, biotin, or a derivative thereof may be used. As for the ligand as described above, the whole ligand may be used, however, a fragment obtained by, for example, an enzymatic treatment may be used. Further, an artificially synthesized peptide, a peptide derivative, or a recombinant may be used.

As the ligand suitable for the separation or purification of immunoglobulin, a protein containing an immunoglobulin binding domain can be mentioned. As the immunoglobulin binding domain, one or more of immunoglobulin binding domains selected from the group consisting of an immunoglobulin binding domain of protein A, an immunoglobulin binding domain of protein G, and an immunoglobulin binding domain of protein L are preferred. In addition, the ligand may have multiple immunoglobulin binding domains that are the same kind as or different kind from one another.

Among the ligands described above, one or more selected from the group consisting of protein A, protein G, protein L, and a functional variant thereof are preferred one or more selected from the group consisting of protein A, protein G, and protein L, are more preferred, and protein A is particularly preferred.

The amount of bound ligands is appropriately adjusted depending on, for example, the kind of the ligand, or the kind of the target substance, and is preferably 10 to 200 mg, and more preferably 25 to 100 mg per 1 g of particles in a case where a protein containing an immunoglobulin binding domain such as protein A is bound as a ligand. In a case where a protein containing an immunoglobulin binding domain is bound as a ligand, when the amount of bound ligands per 1 g of particles is 10 mg or more, the dynamic binding capacity becomes excellent. On the other hand, when the amount of bound ligands per 1 g of particles is 200 mg or less, the amount of the dissociation solution used for dissociating, for example, bound antibodies becomes an appropriate amount.

Further, the carrier of the present invention is excellent in the reduction in the amount of non-specific adsorption.

Moreover, the carrier of the present invention has high mechanical strength, and high dynamic binding capacity of a target substance.

The carrier of the present invention is useful as a carrier for separation of a target substance. In addition, the carrier of the present invention is useful as a carrier for adsorbing body fluid perfusion. In particular, the carrier of the present invention is useful as an affinity-type carrier.

Examples of the target substance include an antigen; an antibody such as a monoclonal antibody, and a polyclonal antibody; cells (normal cells, and cancer cells such as colon cancer cells, and circulating cancer cells in the blood); a nucleic acid such as DNA, and RNA; and a bio-related substance such as a protein, a peptide, amino acid, sugar, polysaccharide, lipid, and vitamin, and the target substance may also be a drug that serves as a potential drug target, or a low-molecular compound such as biotin. In addition, the target substance may be a substance that has been labeled with, for example, a fluorescent substance.

[Column]

The column of the present invention is a column obtained by packing a column container with the carrier of the present invention.

The column of the present invention can be used for detection or separation of a target substance, or for body fluid perfusion adsorption. In particular, the column of the present invention is suitable, for example, for use in affinity chromatography, or for use as a column for whole blood perfusion type extracorporeal circulation.

In addition, examples of the body fluid include a component of blood composition such as whole blood, serum, blood plasma, blood components, various blood cells, and platelet, and further urine, semen, breast milk, sweat, interstitial fluid, interstitial lymph fluid, bone marrow aspirate, tissue fluid, saliva, gastric juice, synovial fluid, pleural effusion, bile, ascite, and amniotic fluid.

[Method for Separating Target Substance]

The method for separating a target substance of the present invention is characterized by using the carrier of the present invention.

The method for separating a target substance of the present invention may be performed according to a conventional method except that the carrier of the present invention is used. For example, a method including a step (contact step) of bringing the carrier of the present invention and a sample containing a target substance into contact with each other by, for example, mixing the carrier and the sample, and a step (separation step) of separating the carrier that has captured the target substance from the sample can be mentioned. In this regard, after the separation step, a step of dissociating the ligand from the target substance may be included.

In addition, the sample may be any sample that contains a target substance or has a possibility of containing a target substance. For example, a body fluid, a microbial cell solution, a medium for cell culture, a cell culture supernatant, a liquid containing disrupted tissue cells, and a buffer solution containing a target substance can be mentioned.

Subsequently, according to the separation method of the present invention, a target substance can be selectively and efficiently separated.

[Method for Producing Porous Particle]

As the method for producing a porous particle of the present invention, for example, a method including the following steps 1 and 2 can be mentioned.

(step 1) A step of dissolving at least one or more of polymers selected from the group consisting of a vinyl alcohol polymer and an ethylene-vinyl alcohol copolymer in an aqueous solvent to prepare a polymer solution.

(step 2) A step of dispersing the above polymer solution in a non-aqueous solvent to form a W/O emulsion.

(Step 1)

Step 1 is a step of dissolving one or more of polymers selected from the group consisting of a vinyl alcohol polymer and an ethylene-vinyl alcohol copolymer (one or more of polymers selected from the group consisting of a vinyl alcohol polymer and an ethylene-vinyl alcohol copolymer are also collectively referred to as a "raw material polymer α") in an aqueous solvent to prepare a polymer solution. As the vinyl alcohol polymer, or ethylene-vinyl alcohol copolymer, one that induces the above-described porous particle of the present invention may be used. In this regard, in the step 1, as the raw material for the porous particle of the present invention, in addition to the vinyl alcohol polymer and the ethylene-vinyl alcohol copolymer, other polymers (for example, polyvinyl pyrrolidone) or a monomer thereof may be used in combination the use amount of the one or more of polymers selected from the group consisting of a vinyl alcohol polymer and an ethylene-vinyl alcohol copolymer is preferably 85 to 100% by mass, more preferably 90 to 100% by mass, furthermore preferably 95 to 100% by mass, and particularly preferably 99 to 100% by mass, relative to the total amount of the compound that gives repeating units to the porous particle.

As the step 1, a step of dissolving an ethylene-vinyl alcohol copolymer in an aqueous solvent to prepare a polymer solution is preferred. By using an ethylene-vinyl alcohol copolymer, the dynamic binding capacity and the target substance capturing performance in a case where a ligand is bound are improved. Further, the exclusion limit molecular weight at which a porous particle becomes suitable for the use in a carrier after a ligand is bound is obtained, and further, the crystal structure is easily formed and the mechanical strength is improved.

The use amount (polymer concentration) of the raw material polymer α used in the step 1 is preferably 0.1% by mass or more, more preferably 1% by mass or more, and particularly preferably 3% by mass or more; and further is preferably 25% by mass or less, more preferably 15% by mass or less, and particularly preferably 10% by mass or less, relative to the total use amount of the raw material polymer α and the aqueous solvent. By setting the use amount of the raw material polymer α to 3% by mass or more, the granulation is easily performed, and on the other hand, by setting the use amount of the raw material polymer α to 15% by mass or less, a sufficiently large pore size is easily secured. In addition, by setting the use amount of the raw material polymer α to 10% by mass or less, the dynamic binding capacity is significantly improved in a case where a ligand is bound to a porous particle.

In the present specification, the expression "aqueous solvent" represents a concept including water, a solvent miscible with water, or a mixed solvent containing thereof.

Examples of the aqueous solvent include water; a solvent miscible with water among sulfoxide-based solvents, such as dimethyl sulfoxide; a solvent miscible with water among polyol-based solvents, such as ethylene glycol; a solvent miscible with water among alcohol-based solvents, such as isopropanol; and a solvent miscible with water among amide-based solvents, such as dimethylformamide. These may be used singly or in combination of more thereof.

Among them, from the viewpoint of the crystallization rate, a mixed solvent containing one or more (hereinafter, also referred to as a "solvent a") selected from the group consisting of a solvent miscible with water among sulfoxide-based solvents, a solvent miscible with water among polyol-based solvents, a solvent miscible with water among alcohol-based solvents, and a solvent miscible with water among amide-based solvents, and water, and water are preferred; a mixed solvent containing one or more selected from the group consisting of dimethyl sulfoxide, ethylene glycol, isopropanol, and dimethylformamide, and water, and water are more preferred; and a mixed solvent containing dimethyl sulfoxide and water is particularly preferred.

In a case where a mixed solvent containing a solvent a and water, the use amount of the solvent a is preferably 40% by mass or more, more preferably 45% by mass or more, and furthermore preferably 50% by mass or more; and further is preferably less than 90% by mass, more preferably less than 80% by mass, and furthermore preferably less than 70% by mass, relative to the total amount of the mixed solvent.

The temperature at which the raw material polymer α is dissolved in the step 1 is, from the viewpoint of facilitating the disintegration of the crystal part of the raw material polymer α, preferably 70° C. or more, more preferably 80° C. or more, and particularly preferably 90° C. or more, and further is preferably 100° C. or less.

In addition, the time to dissolve the raw material polymer α in the step 1 is not particularly limited, and usually around 0.1 to 24 hours.

(Step 2)

Step 2 is a step of dispersing the above polymer solution in a non-aqueous solvent to form a W/O emulsion. By forming the W/O emulsion, the crystal structure can be easily obtained, and the mechanical strength can be improved. In addition, the dynamic binding capacity in a case where a ligand is bound can be increased, and further, the amount of non-specific adsorption can be reduced.

The non-aqueous solvent is not particularly limited as long as it can disperse the polymer solution to form a W/O emulsion, and a non-aqueous solvent immiscible with water is usually used.

Examples of the non-aqueous solvent include a hydrocarbon-based solvent such as an aliphatic hydrocarbon-based solvent, an aromatic hydrocarbon-based solvent, an alicyclic hydrocarbon-based solvent, and a halogenated hydrocarbon-based solvent. These may be used singly or in combination of more thereof. Specifically, for example, hexane, heptane, octane, isooctane, nonane, methylcyclohexane, kerosene, liquid paraffin, benzene, toluene, chloroform, carbon tetrachloride, dichloroethane, dichloromethane, ortho-dichlorobenzene, para-dichlorobenzene, and meta-dichlorobenzene can be mentioned.

The use amount of the non-aqueous solvent is usually around 30 to 200 parts by mass, and preferably 50 to 150 parts by mass, relative to 100 parts by mass of the polymer solution.

The step 2 may be performed in the presence of a dispersant Examples of the dispersant include various kinds of surfactants; polyoxyalkylenes such as polyethylene glycol, and polypropylene glycol; polyvinyl ethers such as polyvinyl methyl ether, and polyvinyl ethyl ether; poly alkyl (meth)acrylates such as poly 2-ethylhexyl (meth)acrylate, poly lauryl (meth)acrylate, and poly stearyl (meth)acrylate; a polymer dispersant soluble in an aqueous solvent such as polyvinyl pyrrolidone, and poly(meth)acrylamide; and a polymer dispersant soluble in a non-aqueous solvent including a polymer of higher fatty acid vinyl ester such as polyvinyl versatate, and polyvinyl 2-ethylhexanoate. These may be used singly or in combination of more thereof.

Among them, a surfactant is preferred, and a nonionic surfactant such as sorbitan fatty acid ester, polyoxyethylene alkyl ester, polyoxyethylene alkyl ether, polyoxyethylene alkyl phenyl ether, and polyoxyethylene sorbitan fatty acid ester are more preferred.

The use amount of the dispersant is usually around 1 to 30 parts by mass, and preferably 5 to 20 parts by mass, relative to 100 parts by mass of the non-aqueous solvent.

In addition, the technique for forming the W/O emulsion is not particularly limited, and it is preferred to form a W/O emulsion by mixing and stirring the polymer solution and the non-aqueous solvent. In this way, a W/O emulsion can be easily formed without using any special equipment.

The dispersion temperature in the step 2 may be appropriately selected in the temperature range of the boiling point or less of the solvent, and usually 2 to 95° C., and preferably 25 to 90° C. In addition, the dispersion time is not particularly limited, and usually 0.1 to 2 hours, and preferably 0.5 to 1 hour.

(Step 3)

As the method for producing a porous particle of the present invention, a method in which a step of cooling the W/O emulsion formed in the step 2 to form porous particles (step 3) is further included is preferred. By the cooling in the step 3, the crystallization of the W/O emulsion is promoted, and the mechanical strength of the porous particle is improved. In addition, the pores of the porous particle to be obtained are easily formed in a desired size.

The cooling in the step 3 may be performed at a temperature relatively lower than the dispersion temperature in the step 2, and the cooling temperature is preferably 0° C. or more from the viewpoint of promoting the crystallization; and further is, from the viewpoint of the crystallization rate and the granulation, preferably 20° C. or less, more preferably 10° C. or less, and particularly preferably 5° C. or less.

In addition, the cooling time is not particularly limited, and usually around 0.5 to 12 hours, and preferably 1 to 5 hours.

In addition, from the viewpoint of the mechanical strength of the particle, after the cooling, it is preferred to heat the inside of the system to the temperature range exceeding 20° C. and 40° C. or less. The heating time is usually around 0.5 to 3 hours, and preferably 1 to 2 hours.

(Step 4)

As the method for producing a porous particle of the present invention, a method in which a step of chemically crosslinking the porous particle formed in the step 3 (step 4) is further included is preferred. By the step 4, the mechanical strength of the porous particle to be obtained is further improved.

The chemical crosslinking may be performed, for example, by using a crosslinking agent, according to a known method (see, for example, JP 2005-171040 A).

As the crosslinking agent, the above-described crosslinking agent may be used as one giving a chemically crosslinked structure.

The use amount of the crosslinking agent is usually around 25 to 300 parts by mass, and preferably 50 to 150 parts by mass, relative to 100 parts by mass (dry particle mass) of the porous particles obtained in the step 3.

In a case where an aldehyde compound is used as the crosslinking agent, the chemical crosslinking is preferably performed in the presence of an acid catalyst. Examples of the acid catalyst include an inorganic acid such as hydrochloric acid, nitric acid, sulfuric acid, and phosphoric acid; and an organic acid such as oxalic acid, and acetic acid, and an inorganic acid is preferred, and sulfuric acid is particularly preferred. Further, these acid catalysts may be used singly or in combination of more thereof.

From the viewpoint of the mechanical strength, the use amount of the acid catalyst is usually 1 to 200 parts by mass, and preferably 10 to 100 parts by mass, relative to 100 parts by mass of the aldehyde compound.

It is preferred to perform the step 4 in the presence of a solvent. As the solvent, a solvent that dissolves a crosslinking agent without dissolving a raw material polymer α is preferred. Specific examples of the solvent include water; an alcohol-based solvent such as methanol, ethanol, propanol, butanol, pentanol, hexanol, and glycerin; and a mixed solvent thereof. Among them, in view of the ease of the industrial application, water, ethanol, and a mixed solvent thereof are preferred.

The use amount of the solvent is usually around 500 to 5000 parts by mass, and preferably 1000 to 4000 parts by mass, relative to 100 parts by mass (dry particle mass) of the porous particles obtained in the step 3.

The reaction temperature of the step 4 is usually 40 to 70° C. In addition, the reaction time of the step 4 is not particularly limited, and usually around 3 to 24 hours.

(Step 5)

The method for producing a porous particle of the present invention may further include a step of bringing the porous particle chemically crosslinked in the step 4 and one or more of polymers selected from the group consisting of a vinyl alcohol polymer and an ethylene-vinyl alcohol copolymer into contact with each other (step 5). In a case where an aldehyde compound is used as the crosslinking agent in the step 4, by the step 5, the hydroxy group in the repeating unit (2) contained in the vinyl alcohol polymer or the ethylene-vinyl alcohol copolymer and the remaining formyl group of the porous particle react with each other, therefore, blocking of the remaining formyl group of the porous particle can be caused.

As the above vinyl alcohol polymer or ethylene-vinyl alcohol copolymer, one similar to the vinyl alcohol polymer or ethylene-vinyl alcohol copolymer that is used as a raw material polymer in the present invention can be mentioned. Further, the use amount of the vinyl alcohol polymer and the ethylene-vinyl alcohol copolymer is usually around 5 to 75 parts by mass, and preferably 10 to 50 parts by mass, relative to 100 parts by mass (dry particle mass) of the porous particles chemically crosslinked in the step 4.

It is preferred to perform the step 5 in the presence of an acid catalyst and a solvent. As the acid catalyst and the solvent, ones similar to the acid catalyst and the solvent in the step 4 can be mentioned.

The reaction temperature in the step 5 is usually 40 to 70° C. In addition, the reaction time of the step 5 is not particularly limited, and usually around 1 to 24 hours.

(Step 6)

The method for producing a porous particle of the present invention may further include a step of introducing a reactive functional group capable of binding to a ligand into the porous particle formed in the step 3, the porous particle chemically crosslinked in the step 4, or the porous particle to which blocking is applied in the step 5 (step 6) (in the step 6, these are collectively referred to as a "porous particle Z").

The introduction of the reactive functional group may be performed according to a conventional method, and in a case where an epoxy group is introduced as the reactive functional group, as the technique, a technique for bringing a porous particle Z and an epoxy compound into contact with each other is preferred. The epoxy compound to be used here is a compound further having one or more epoxy groups in addition to the functional group (for example, an epoxy group, or a halogen atom) that reacts with the hydroxyl group in the repeating unit (2) contained in a raw material polymer. Examples of the epoxy compound as described above include epihalohydrin such as epichlorohydrin, epibromohydrin, epifluorohydrin, and epiiodohydrin; bifunctional bisepoxides such as ethylene glycol diglycidyl ether, neopentyl glycol diglycidyl ether, resorcinol diglycidyl ether, hydrogenated bisphenol A diglycidyl ether, glycerol diglycidyl ether, trimethylolpropane diglycidyl ether, diethylene glycol diglycidyl ether, and propylene glycol diglycidyl ether; and a tri- or more-functional epoxy compound such as glycerol polyglycidyl ether, trimethylolpropane polyglycidyl ether, pentaerythritol polyglycidyl ether, diglycerol polyglycidyl ether, polyglycerol polyglycidyl ether, and sorbitol polyglycidyl ether. These may be used singly or in combination of more thereof.

The step 6 may be performed in the presence of a salt such as sodium chloride, or sodium sulfate, as needed. Further, it is preferred to perform the step 6 in the presence of a solvent. As the solvent, one similar to the solvent in the step 4 can be mentioned.

The reaction temperature of the step 6 is usually 20 to 37° C. In addition, the reaction time of the step 6 is not particularly limited, and usually around 0.5 to 12 hours.

In addition, in the above steps 3 to 6, the isolation of each product may be performed by appropriately combining ordinary means such as filtration, washing, drying, recrystallization, reprecipitation, dialysis, centrifugation, extraction with various kinds of solvents, neutralization, and chromatography, as needed.

In addition, according to the method for producing a porous particle of the present invention, the porous particle of the present invention, with which non-specific adsorption is hardly generated although the porous particle is a synthetic polymer-based particle, and which is useful as a support material or a support of a carrier, can be simply and easily produced. Further, the porous particle obtained in this production method has high mechanical strength, and high dynamic binding capacity in a case where a ligand is bound.

EXAMPLES

Hereinafter, the present invention will be described in detail with reference to Examples, however, the present invention is not limited to the following Examples.

Synthesis Example 1: Synthesis of Ethylene-vinyl Alcohol Copolymer

Into a high-pressure autoclave, 100 parts by mass of vinyl acetate, and 50 parts by mass of methanol were charged, the temperature was raised to 60° C., and then the system was purged with nitrogen gas by nitrogen bubbling for 30 minutes. Azobisisobutyronitrile is dissolved in methanol to prepare a methanol solution of a polymerization initiator (polymerization initiator solution) having a concentration of 0.4% by mass, and then nitrogen purge was conducted by bubbling nitrogen gas. After the reaction vessel was thoroughly purged with ethylene, the internal temperature of the reaction vessel was adjusted to 60° C., and 67 parts by mass of the polymerization initiator solution was injected to initiate polymerization. During the polymerization, the ethylene pressure in the reaction vessel was maintained at 1.57 MPa, and the polymerization temperature was maintained at 50° C. After the lapse of 6 hours, the polymerization was terminated by cooling. The reaction vessel was opened to release the ethylene, and then nitrogen gas was bubbled to remove the ethylene. Next, unreacted vinyl acetate was removed under reduced pressure, and then a methanol solution of the copolymer was obtained.

A NaOH methanol solution (10% by mass) having a mole ratio (the number of moles of NaOH/the number of moles of polyvinyl acetate) of 0.05 was added to the copolymer solution adjusted to 10% by mass, the resultant mixture was maintained at 40° C., and the saponification reaction was conducted for 2 hours. The methanol solution of the copolymer, which had been obtained by removing unreacted vinyl acetate monomers after the polymerization, was poured into normal hexane to precipitate the copolymer, reprecipitation purification by dissolving the recovered copolymer with acetone was conducted 3 times, and then the resultant product was dried at 60° C. under reduced pressure to obtain a purified product of the copolymer.

In the obtained ethylene-vinyl alcohol copolymer, when the molar ratio between the repeating unit (1) derived from ethylene and the repeating unit (2) derived from vinyl alcohol was measured by proton NMR, the molar ratio was 15:85. In addition, the polymerization degree calculated in accordance with JIS K 6726 was 400, and the saponification degree measured in accordance with JIS K 6726 was 99% by mole.

Synthesis Example 2: Synthesis of Ethylene-vinyl Alcohol Copolymer

An ethylene-vinyl alcohol copolymer was synthesized in a similar manner as in Synthesis Example 1 except that the ethylene pressure in the reaction vessel during the polymerization was changed to 0.60 MPa.

In the obtained ethylene-vinyl alcohol copolymer, when the molar ratio between the repeating unit (1) derived from ethylene and the repeating unit (2) derived from vinyl alcohol was measured by proton NMR, the molar ratio was 5:95. In addition, the polymerization degree calculated in accordance with JIS K 6726 was 400, and the saponification degree measured in accordance with JIS K 6726 was 99% by mole.

Preparation Example 1: Preparation of Protein A-bound Porous Particle

<Particle Preparation>

Into a 7 L separable flask with baffle, 100 parts by mass of the ethylene-vinyl alcohol copolymer obtained in Synthesis Example 1, 827 parts by mass of dimethyl sulfoxide (manufactured by Wako Pure Chemical Industries, Ltd.), and 502 parts by mass of distilled water were charged, and the resultant mixture was heated at 95° C. for 0.5 hour while stirring the mixture at 100 rpm to dissolve the ethylene-vinyl alcohol copolymer. This solution was taken as an ethylene-vinyl alcohol copolymer solution L. Further, the concentration of the ethylene-vinyl alcohol copolymer in this solution was 7% by mass.

Next, the copolymer solution L was cooled down to 80° C., and into the cooled solution L, a solution including 143 parts by mass of SPAN-80 (manufactured by TOKYO CHEMICAL INDUSTRY CO., LTD.) and 1287 parts by mass of isooctane (manufactured by Wako Pure Chemical Industries, Ltd.), which had been separately prepared, was added, and the resultant mixture was stirred at 125 rpm to prepare a W/O emulsion. The W/O emulsion was cooled down in the vicinity of 0° C. over around 30 to 50 minutes, and retained for around 2 to 4 hours, and then the temperature was raised to room temperature, and by continuously stirring the mixture for 1 hour, the copolymer was made into a spherical shape. After that, the reaction mixture was washed with 4000 parts by mass of ethanol under stirring, and the particle layer was recovered by suction filtration. This porous particle is taken as a "particle A".

Crosslinking Reaction>

The recovered particles A in an amount of 100 parts by mass (in terms of dry particle mass) was dispersed in 2399 parts by mass of ethanol, and then into the resultant dispersion, 43 parts by mass of a 47% by mass sulfuric acid aqueous solution and 500 parts by mass of a 20% by mass aqueous glutaraldehyde solution (manufactured by Wako Pure Chemical Industries, Ltd.) were added, and the crosslinking reaction was performed at 60° C. for 6 to 9 hours. After that, the resultant product was washed with 5000 parts by mass of water, and the particle layer was recovered by suction filtration. The porous particle crosslinked with glutaraldehyde is taken as a "particle B".

<Blocking>

Particles B in an amount of 100 parts by mass (in terms of dry particle mass) were dispersed in 2600 parts by mass of water, and into the resultant dispersion, 11 parts by mass of a 47% by mass sulfuric acid aqueous solution, and 400 parts by mass of a 5% by mass aqueous solution of the ethylene-vinyl alcohol copolymer obtained in Synthesis Example 1 were added, and then the resultant mixture was heated to 50° C., and the reaction was conducted for around 1 to 3 hours. After that, the resultant product was filtered by Nutsche, washed with water, and the particles were recovered. The porous particle to which blocking was applied is taken as a "particle C".

<Epoxy group Introduction>

Sodium sulfate in an amount of 100 parts by mass, 24 parts by mass of sodium dihydrogenphosphate, and 36 parts by mass of a 50% by mass aqueous sodium hydroxide solution were added into 1876 parts by mass of water to prepare a buffer for epoxy group introduction. Into the buffer for epoxy group introduction in an amount of 4750 parts by mass, 100 parts by mass (in terms of dry particle mass) of particles C, and 1500 parts by mass of ethylene glycol diglycidyl ether (manufactured by Wako Pure Chemical Industries, Ltd.) were added, and the resultant mixture was reacted at room temperature for 2 hours. After that, the resultant product was filtered by Nutsche, washed with water, and the epoxy group-introduced porous particles were recovered. The epoxy group-introduced porous particle is taken as a "particle D".

<Immobilization of Protein A>

The epoxy group-introduced porous particles D in an amount of 100 parts by mass (in terms of dry particle mass), 600 parts by mass of a solution (solvent: phosphate buffer) of 48.68 mg/mL protein A (prepared by the method described in Examples in WO 2015/080174 A), and 8100 parts by mass of a 1 M citrate buffer (pH 12) were mixed, and the resultant mixture was mingled by inversion at 25° C. for 5 hours to bind the protein A to the epoxy group-introduced porous particles D. The formed particles were filtered, and then mixed with 7500 parts by mass of a 1 M thioglycerol aqueous solution, and the resultant mixture was reacted at 25° C. for 12 hours. Next, the particles were washed with 15000 parts by mass of a 0.1 M phosphate buffer (pH 7.6), 15000 parts by mass of a 0.5 M NaOH aqueous solution, and 15000 parts by mass of a 0.1 M citrate buffer (pH 3.2) to obtain desired protein A-bound porous particles. The protein A-bound porous particle is taken as a "carrier A".

Preparation Example 2: Preparation of Protein A-bound Porous Particle

Except that 100 parts by mass of the ethylene-vinyl alcohol copolymer that had been used in the step of <Particle preparation> was changed to 85 parts by mass of the ethylene-vinyl alcohol copolymer (the molar ratio of repeating units (1) derived from ethylene and repeating units (2) derived from vinyl alcohol=5:95) obtained in Synthesis Example 2, and the ethylene-vinyl alcohol copolymer that had been used in the step of <Blocking> was changed to the ethylene-vinyl alcohol copolymer obtained in Synthesis Example 2, protein A-bound porous particles were prepared in a similar procedure as in Preparation Example 1. Note that the concentration of the ethylene-vinyl alcohol copolymer in the ethylene-vinyl alcohol copolymer solution in the step of <Particle preparation> was 6% by mass.

The porous particle obtained in Preparation Example 2, to which blocking was applied, is taken as a "particle E". Further, the protein A-bound porous particle obtained in Preparation Example 2 is taken as a "carrier B".

Preparation Example 3: Preparation of Protein A-Bound Porous Particle

Except that 100 parts by mass of the ethylene-vinyl alcohol copolymer that had been used in the step of <Particle preparation> was changed to 85 parts by mass of the ethylene-vinyl alcohol copolymer (EVAL L171B manufactured by KURARAY CO., LTD.) having a molar ratio of repeating units (1) derived from ethylene and repeating units (2) derived from vinyl alcohol of 27:73, and the ethylene-vinyl alcohol copolymer that had been used in the step of <Blocking> was changed to EVAL L171B manufactured by KURARAY CO., LTD., protein A-bound porous particles were prepared in a similar procedure as in Preparation Example 1. Note that the concentration of the ethylene-vinyl alcohol copolymer in the ethylene-vinyl alcohol copolymer solution in the step of <Particle preparation> was 6% by mass.

The porous particle obtained in Preparation Example 3, to which blocking was applied, is taken as a "particle F". Further, the protein A-bound porous particle obtained in Preparation Example 3 is taken as a "carrier C".

Preparation Example 4: Preparation of Protein A-bound Porous Particle

Except that 100 parts by mass of the ethylene-vinyl alcohol copolymer that had been used in the step of <Particle preparation> was changed to 85 parts by mass of the ethylene-vinyl alcohol copolymer (EVAL H171B manufactured by KURARAY CO., LTD.) having a molar ratio of repeating units (1) derived from ethylene and repeating units (2) derived from vinyl alcohol of 38:62, and the ethylene-vinyl alcohol copolymer that had been used in the step of <Blocking> was changed to EVAL H171B manufactured by KURARAY CO., LTD., protein A-bound porous particles were prepared in a similar procedure as in Preparation Example 1. Note that the concentration of the ethylene-vinyl alcohol copolymer in the ethylene-vinyl alcohol copolymer solution in the step of <Particle preparation> was 6% by mass.

The porous particle obtained in Preparation Example 4, to which blocking was applied, is taken as a "particle G".

Further, the protein A-bound porous particle obtained in Preparation Example 4 is taken as a "carrier D".

Preparation Example 5: Preparation of Protein A-bound Porous Particle

Except that 100 parts by mass of the ethylene-vinyl alcohol copolymer that had been used in the step of <Particle preparation> was changed to 85 parts by mass of the ethylene-vinyl alcohol copolymer (EVAL G1565 manufactured by KURARAY CO., LTD.) having a molar ratio of repeating units (1) derived from ethylene and repeating units (2) derived from vinyl alcohol of 44:56, and the ethylene-vinyl alcohol copolymer that had been used in the step of <Blocking> was changed to EVAL G156B manufactured by KURARAY CO., LTD., protein A-bound porous particles were prepared in a similar procedure as in Preparation Example 1. Note that the concentration of the ethylene-vinyl alcohol copolymer in the ethylene-vinyl alcohol copolymer solution in the step of <Particle preparation> was 6% by mass.

The porous particle obtained in Preparation Example 5, to which blocking was applied, is taken as a "particle H". Further, the protein A-bound porous particle obtained in Preparation Example 5 is taken as a "carrier E".

Preparation Example 6: Preparation of Protein A-bound Porous Particle

Except that 100 parts by mass of the ethylene-vinyl alcohol copolymer that had been used in the step of <Particle preparation> was changed to 85 parts by mass of polyvinyl alcohol (JF-04 manufactured by JAPAN VAM & POVAL CO., LTD., saponification degree: 98%), and the ethylene-vinyl alcohol copolymer that had been used in the step of <Blocking> was changed to JF-04 manufactured by JAPAN VAM & POVAL CO., LTD., protein A-bound porous particles were prepared in a similar procedure as in Preparation Example 1. Note that the concentration of the polyvinyl alcohol in the polyvinyl alcohol solution in the step of <Particle preparation> was 6% by mass.

The porous particle obtained in Preparation Example 6, to which blocking was applied, is taken as a "particle I". Further, the protein A-bound porous particle obtained in Preparation Example 6 is taken as a "carrier F".

Comparative Preparation Example 1: Preparation of Protein A-Bound Porous Particle Protein A-bound porous particles obtained by using methacrylate as a raw material were prepared as follows.

Into 4090 parts by mass of pure water, 8.5 parts by mass of polyvinyl alcohol (PVA-217 manufactured by KURARAY CO, LTD.) 2.13 parts by mass of sodium dodecyl sulfate (EMAL 10G manufactured by Kao Corporation), and 4.26 parts by mass of sodium carbonate were added, and the resultant mixture was stirred overnight to prepare an aqueous solution (S-1).

The aqueous solution (S-1) in an amount of 30 parts by mass was separately taken out, and in the remaining aqueous solution (S-1), 2.13 parts by mass of sodium nitrite was dissolved to prepare an aqueous solution (S-2).

Next, 125 parts by mass of glycerin dimethacrylate (manufactured by Shin Nakamura Chemical Co., Ltd.), 17.9 parts by mass of glycidyl methacrylate (manufactured by Mitsubishi Rayon Co., Ltd.), and 35.9 parts by mass of glycerol monomethacrylate (manufactured by Nippon Oil & Fats Co., Ltd.) were dissolved in a mixture of 86.4 parts by mass of 2-octanone (manufactured by Toyo Gosei Co., Ltd) and 253 parts by mass of acetophenone (manufactured by Wako Pure Chemical Industries, Ltd.), to prepare a monomer solution. In addition, in the whole amount of this monomer, glycerin dimethacrylate was 70% by mass, glycidyl methacrylate was 10% by mass, and glycerol monomethacrylate was 20% by mass.

Subsequently, into the 30 parts by mass of aqueous solution (S-1) that had been taken out, 2.2 parts by mass of 2,2'-azoisobutyronitrile (manufactured by Wako Pure Chemical Industries, Ltd.) was added and dispersed to prepare an initiator dispersion.

Next, the prepared aqueous solution (S-2) and a monomer solution were charged into a 7 L separable flask with baffle, and a thermometer, a stirring blade, and a cooling pipe were attached to the separable flask, then the flask was set in a warm water bath, and the stirring was started at 220 rpm under a nitrogen atmosphere. Subsequently, the separable flask was heated with a warm water bath, and when the temperature reached 85° C., the above initiator dispersion was added, and the resultant mixture was stirred for 5 hours while maintaining the temperature at 85° C. Next, after cooling the reaction mixture, the reaction mixture was filtered by Nutsche, and the washing was performed with pure water and isopropyl alcohol. The washed particles were transferred to a plastic bottle, and dispersed in water, and the resultant dispersion was decanted 3 times to remove small particles. According to the process described above, 12.5% by mass of porous particles (dry particle mass: 123 g) dispersed in water were obtained. The porous particle is taken as a "particle J".

Herein, the epoxy group content of the particle J was measured. That is, an aqueous dispersion (known concentration) of the particles J having a concentration of around 10% by mass was weighed into a polyethylene bottle so that the number of moles of the epoxy groups calculated from the amount of the epoxy group-containing monomer used in the polymerization is 2.00 mmol and into this aqueous dispersion, 25 mL of an aqueous calcium chloride solution having a concentration of 38% by mass and 2.00 mL of 2 N hydrochloric acid were added, the resultant mixture was stirred at 75° C. for 150 minutes for ring opening of the epoxy group, then after cooling, 2.50 mL of a 2 N aqueous sodium hydroxide solution was added for the neutralization, and further, back titration was performed with 0.1 N hydrochloric acid while monitoring the pH with a pH meter to measure the epoxy group content. As a result of the measurement, the epoxy group content of particle J was 0.47 mmol/g.

Next, 0.1 part by mass of protein A was dispersed in 25 parts by mass of a 0.1 M phosphate buffer (pH 6.8), this dispersion and 1 part by mass of particles J in terms of dry particle mass were mixed, and the mixture was mingled by inversion at 10° C. for 24 hours to bind the protein A to the particles J. After filtering the formed particles, the particles were mixed with 25 parts by mass of 1 M thioglycerol, the mixture was reacted at 30° C. for 4 hours for ring opening of the remaining epoxy groups, and the washing was performed with PBS/0.5% by mass Tween 20, then further performed with PBS. The obtained porous particle is taken as a "carrier G".

Comparative Preparation Example 2: Preparation of Protein A-Bound Particle

The ethylene-vinyl alcohol copolymer (EVAL L171B manufactured by KURARAY CO., LTD.) having a molar ratio of repeating units (1) derived from ethylene and repeating units (2) derived from vinyl alcohol of 27:73 in an amount of 100 parts by mass was dissolved in 1570 parts by mass of dimethyl sulfoxide (manufactured by Wako Pure Chemical Industries, Ltd.) while stirring to prepare a polymer solution. Further, the concentration of the ethylene-vinyl alcohol copolymer in this solution was 6% by mass.

Next, the above polymer solution was discharged from a nozzle having an inner diameter of 150 μm so as to be added in solidified water dropwise, and polymer particles were obtained.

Subsequently, the obtained polymer particles were treated in a similar manner as in the <Crosslinking reaction>, <Blocking>, <Epoxy group introduction>, and <Immobilization of protein A> of Preparation Example 1. Further, the step of <Blocking> was performed by changing the 2600 parts by mass of water to 2600 parts by mass of dimethyl sulfoxide, and the 400 parts by mass of a 5% by mass aqueous solution of the ethylene-vinyl alcohol copolymer obtained in Synthesis Example 1 to 400 parts by mass of a 5% by mass dimethyl sulfoxide solution of EVAL L171B manufactured by KURARAY CO., LTD, respectively.

The particle obtained in Comparative Preparation Example 2, to which blocking was applied, is taken as a "particle K". Further, the protein A-bound particle obtained in Comparative Preparation Example 2 is taken as a "carrier H".

Test Example 1: X-Ray Diffraction

The particles A obtained in Preparation Example 1 were dispersed in water to obtain a slurry, and this slurry was replaced with a t-butyl alcohol solution, and then the resultant slurry was frozen in a freezer for 30 minutes, then dried in a vacuum dryer for 3 hours to obtain dry particle powder. This dry particle powder was ground using a mortar and a pestle, and the powder X-ray diffraction pattern was confirmed using an X-ray diffraction device SmartLab (manufactured by Rigaku Corporation). With respect to the particles B to C and carrier A prepared in Preparation Example 1, the powder X-ray diffraction pattern was also confirmed in a similar manner. These powder X-ray diffraction patterns are shown in FIG. 1.

Figure 1:
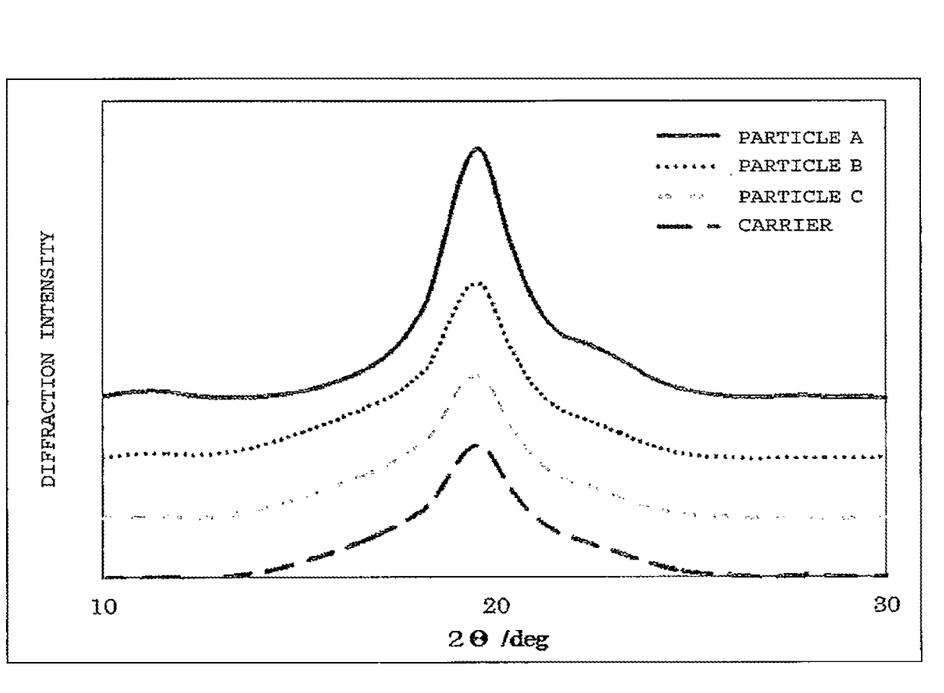
FIG. 1 is a drawing that shows peaks of powder X-ray diffractions of the particles A to C and carrier A obtained in Preparation Example 1.

As shown in FIG. 1, it was confirmed that all of the particles A to C and carrier A had a peak in the vicinity of 2θ 19.4° derived from the crystal structure of vinyl alcohol (see Macromolecules 2004, 37, 1921-1927).

Test Example 2: Distribution Coefficient Kav and Exclusion Limit Molecular Weight Using AKTA prime plus manufactured by GE Healthcare, the distribution coefficient Kav of the particle C obtained in Preparation Example 1 was measured by an elution volume (mL) of the following each marker molecule at a linear flow rate of 300 cm/hr. Further, using the measured Kav, the exclusion limit molecular weight was measured. The column container has a volume of 4 mL (5 mmϕ×200 mm in length), and the markers (1) to (6) were used after being dissolved in a 20 mM sodium phosphate/150 mM sodium chloride aqueous solution (pH 7.5).

Marker (1): Sodium polystyrene sulfonate (manufactured by Sigma-Aldrich Co. LLC., MW: 2,260 kDa)

Marker (2): Carbonic Anhydrase (manufactured by Sigma-Aldrich Co. LLC., approximate molecular mass: 29 kDa)

Marker (3): Albumin (manufactured by Sigma-Aldrich Co. LLC., approximate molecular mass: 66 kDa)

Marker (4): β-amylase (manufactured by Sigma-Aldrich Co. LLC., approximate molecular mass: 200 kDa)

Marker (5): Thyroglobulin (manufactured by Sigma-Aldrich Co. LLC., approximate molecular mass: 669 kDa)

Marker (6): Human Immunoglobulin G (HGG-1000 manufactured by Equitech-Bio, Inc.)

Marker (7): 0.5 M sodium chloride aqueous solution (manufactured by Wako Pure Chemical Industries, Ltd.)

The distribution coefficient Kav was determined by the following equation.

$$Kav=(Ve-Vo)/(Vt-Vo)$$

Ve represents an elution volume of each marker.

Vo represents an elution volume of sodium polystyrene sulfonate.

Vt represents a volume occupied by a packed bed of particles (particle layer volume) when the column container is packed with particles C.

The logarithm of the molecular weight {ln (molecular weight) (MW)} of each marker was plotted on the horizontal axis, and the Kav was plotted on the vertical axis, and then the slope and intercept of the following equation were obtained from the part showing linearity. The molecular weight at which the Kav becomes 0 was calculated from the obtained slope and intercept, and the calculated value was taken as the exclusion limit molecular weight.

$$Kav=(\text{slope})\times\ln(\text{MW})+(\text{intercept})$$

With respect to the particles E to I and K prepared in Preparation Examples 2 to 6 and Comparative Preparation Example 2, the Kav and the exclusion limit molecular weight were also measured in a similar manner. The results of Test Example 2 are shown in Table 2.

Test Example 3: Void Ratio

Using AKTA prime plus (manufactured by GE Healthcare), the particles C obtained in Preparation Example 1 were packed in a column similar to that in Test Example 2, and the void ratio of the particles C was calculated by the following equation.

$$\text{Void ratio }[\%]=(Vi-Vo)/(CV-Vo)\times 100$$

Vi represents an elution volume when a sodium chloride aqueous solution was passed through in Test Example 2.

Vo is as described in Test Example 2.

CV represents a column volume, and a value determined from the diameter of the column and the height of the column.

With respect to the particles E to K prepared in Preparation Examples 2 to 6 and Comparative Preparation Examples 1 to 2, the void ratio was also measured in a similar manner. The results of Test Example 3 are shown in Table 2.

Test Example 4: Bulk Density

The particles C obtained in Preparation Example 1 were dispersed in water to obtain a slurry, and this slurry was poured into a graduated cylinder, and the poured amount was weighed. The measuring flask was left to stand, the slurry was completely settled by gravity, the settled volume was determined, and the bulk density was calculated by the following equation.

Bulk density=poured slurry amount [g]×solid content concentration [% by mass]/settled volume [mL]

In addition, the solid content concentration was determined as follows. The above slurry was poured onto an aluminum dish, and heated with a hot plate at 200° C. to completely remove the moisture. The mass of the solid matter remaining on the aluminum dish was divided by the mass of the slurry, and the determined value was multiplied by 100 to obtain the solid content concentration [% by mass].

With respect to the particles E to K prepared in Preparation Examples 2 to 6 and Comparative Preparation Examples 1 to 2, the bulk density was also measured in a similar manner. The results of Test Example 4 are shown in Table 2.

Test Example 5: Specific Surface Area

Using a mercury porosimeter (AutoPore IV9520 manufactured by Shimadzu Corporation), the specific surface area of the particle C obtained in Preparation Example 1 was calculated in the measurement range of 10 nm to 5000 nm.

With respect to the particles E to K prepared in Preparation Examples 2 to 6 and Comparative Preparation Examples 1 to 2, the specific surface area was also measured in a similar manner. The results of Test Example 5 are shown in Table 2.

Test Example 6: Evaluation of Non-Specific Adsorption

In a column container with a volume of 1 mL (5 mmφ×50 mm in length), the carrier A obtained in Preparation Example 1 was packed so that the packed bed height is around 5 cm. The obtained column was connected to AKTA Prime Plus manufactured by GE Healthcare, and equilibrated with a 20 mM sodium phosphate buffer (pH 7.5).

Next, the CHO cell culture supernatant containing a monoclonal antibody Trastuzumab was passed through the column at a flow rate of 0.2 mL/min.

Subsequently, a 20 mM sodium phosphate buffer (pH 7.5), a 20 mM sodium phosphate/1 M sodium chloride buffer (pH 7.5), and a 20 mM sodium phosphate buffer (pH 7.5) each were sequentially passed through the column with 5 column volumes at a flow rate of 0.2 mL/min.

After that, a 100 mM sodium acetate buffer (pH 3.2) was passed through the column at a flow rate of 0.2 mL/min to elute the monoclonal antibody captured in the column, and eluted fractions having a UV absorbance of 100 mAu at a wavelength of 280 nm were recovered.

Further, the antibody concentration (mg/mL) contained in the recovered fractions was measured using a spectrophotometer. In addition, using a CHO HCP ELISA kit, 3G manufactured by Cygnus Technologies Inc., the concentration (ng/mL) of the host cell proteins (HCPs) contained in the recovered fractions was measured. Further, the amount of HCP per unit amount of antibody was calculated by dividing the concentration of HCP by the antibody concentration, and the non-specific adsorption was evaluated in accordance with the following evaluation criteria.

Evaluation criteria for non-specific adsorption

AA: 2000 ppm/IgG or less
A: Exceeding 2000 ppm/IgG and 3000 ppm/IgG or less
B: Exceeding 3000 ppm/IgG and 4000 ppm/IgG or less
C: Exceeding 4000 ppm/IgG With respect to the carriers B to H prepared in Preparation Examples 2 to 6 and Comparative Preparation Examples 1 to 2, the HCP was also quantified and the non-specific adsorption was also evaluated, in a similar manner. The results of Test Example 6 are shown in Table 3.

(Test Example 7: Measurement of Dynamic Binding Capacity (DBC))

Using a chromatography device AKTA prime plus manufactured by GE Healthcare, the DBC of the carrier A obtained in Preparation Example 1 to proteins (human polyclonal IgG antibody, HGG-1000 manufactured by Equitech-Bio, Inc.) at a linear flow rate of 300 cm/hr was measured. Using a column container with a volume of 4 mL (5 mmφ×200 mm in length) as the column container, and one in which proteins had been dissolved by the concentration of 5.3 mg/mL in a 20 mM sodium phosphate/150 mM sodium chloride aqueous solution (pH 7.5) as the protein, respectively, the DBC was calculated from the amount of the captured proteins at the time when the concentration of human polyclonal IgG in the eluate reached a 10% breakthrough as monitored by an absorbance monitor and the column packing volume, and the DBC was evaluated in accordance with the following evaluation criteria.

Evaluation Criteria for DBC
AA: 55 mg/mL or more and less than 75 mg/mL
A: 45 mg/mL or more and less than 55 mg/mL
B: 25 mg/mL or more and less than 45 mg/mL
C: Less than 25 mg/mL With respect to the carriers B to H prepared in Preparation Examples 2 to 6 and Comparative Preparation Examples 1 to 2, the DBC was also measured in a similar manner. The results of Test Example 7 are shown in Table 3.

(Test Example 8: Evaluation for Mechanical Strength (Measurable Linear Flow Rate)

Using AKTA Avant manufactured by GE Healthcare, ultrapure water was passed through a column container with 16 mmφ×150 mm at a linear flow rate of 300 cm/hr, and the carrier A obtained in Preparation Example 1 was packed so that the packed bed height is around 10 cm. The linear flow rate was increased by 100 cm/hr every 1 minute, and the maximum flow rate at which the pressure applied to the column does not exceed 2 MPa was measured as the measurable linear flow rate.

Evaluation Criteria for Mechanical Strength
A: Measurable linear flow rate is 2000 cm/hr or more
B: Measurable linear flow rate is 1000 cm/hr or more and less than 2000 cm/hr
C: Measurable linear flow rate is less than 1000 cm/hr With respect to the carriers B to H prepared in Preparation Examples 2 to 6 and Comparative Preparation Examples 1 to 2, the measurable linear flow rate was also measured in a similar manner. The results of Test Example 8 are shown in Table 3.

TABLE 1

| | Raw material polymer | | Polymer | | | |
|---|---|---|---|---|---|---|
| | Kind | Ethylene content (% by mole) | concentration (% by mass) | Emulsion during particle preparation | Crystallization (*1) | Chemical crosslinking |
| Preparation Example 1 | EVOH | 15 | 7 | W/O emulsion | Present | Present |
| Preparation Example 2 | EVOH | 5 | 6 | W/O emulsion | Present | Present |
| Preparation Example 3 | EVOH | 27 | 6 | W/O emulsion | Present | Present |
| Preparation Example 4 | EVOH | 38 | 6 | W/O emulsion | Present | Present |
| Preparation Example 5 | EVOH | 44 | 6 | W/O emulsion | Present | Present |
| Preparation Example 6 | PVA | 0 | 6 | W/O emulsion | Present | Present |
| Comparative Preparation Example 1 | MA | 0 | — | — | Absent | Present |
| Comparative Preparation Example 2 | EVOH | 27 | 6 | O/W emulsion | Present | Present |

EVOH: Ethylene-vinyl alcohol copolymer
PVA: Polyvinyl alcohol
MA: Methacrylate-based polymer
(*1): Presence or absence of a crystal structure in porous particle and carrier (Present: both the porous particle and the carrier have a crystal structure, and Absent: both the porous particle and the carrier have no crystal structure)

TABLE 2

| | Kav [—] (IgG) | Exclusion limit molecular weight [KDa] | Void ratio [%] | Bulk density [g/mL] | Specific surface area [m²/g] |
|---|---|---|---|---|---|
| Preparation Example 1 | 0.62 | 1.9 × 10^5 | 92 | 0.11 | 95.2 |
| Preparation Example 2 | 0.61 | 1.7 × 10^5 | 92 | 0.11 | 94.8 |
| Preparation Example 3 | 0.68 | 3.5 × 10^5 | 90 | 0.10 | 94.0 |
| Preparation Example 4 | 0.70 | 4.8 × 10^5 | 88 | 0.10 | 93.9 |
| Preparation Example 5 | 0.72 | 4.9 × 10^5 | 89 | 0.11 | 93.5 |
| Preparation Example 6 | 0.42 | 1.5 × 10^5 | 88 | 0.12 | 82.1 |
| Comparative Preparation Example 1 | — | — | 80 | 0.15 | 80 |
| Comparative Preparation Example 2 | 0.38 | 2.6 × 10^3 | 62 | 0.19 | 77 |

TABLE 3

| | HCP | | DBC | | Measurable linear flow rate | |
|---|---|---|---|---|---|---|
| | [ppm/IgG] | Evaluation | [mg/mL] | Evaluation | [cm/hr] | Evaluation |
| Preparation Example 1 | 1900 | AA | 55 | AA | 2000 | A |
| Preparation Example 2 | 1900 | AA | 52 | A | 2000 | A |
| Preparation Example 3 | 2000 | AA | 58 | AA | 2100 | A |
| Preparation Example 4 | 2200 | A | 60 | AA | 2400 | A |
| Preparation Example 5 | 3000 | A | 45 | A | 2700 | A |
| Preparation Example 6 | 1700 | AA | 30 | B | 2000 | A |
| Comparative Preparation Example 1 | 6500 | C | 36 | B | 900 | C |
| Comparative Preparation Example 2 | 2000 | AA | 10 | C | 2000 | A |

As shown in Tables 1 to 3, in a case where the methacrylate-based polymer was used as the raw material polymer (Comparative Preparation Example 1), the amount of non-specific adsorption was large, and the mechanical strength was poor.

In addition, porous particles having a void ratio of 62% were prepared by forming an O/W emulsion, and in a case of using these particles (Comparative Preparation Example 2), the dynamic binding capacity was small.

On the other hand, in a case where porous particles derived from one or more of polymers selected from the group consisting of a vinyl alcohol polymer and an ethylene-vinyl alcohol copolymer, and having a void ratio of 75% or more were used (Preparation Examples 1 to 6), the amount of non-specific adsorption was small, the dynamic binding capacity was large, and excellent mechanical strength was exhibited. In particular, in the case where using the porous particles obtained by dissolving an ethylene-vinyl alcohol copolymer in an aqueous solvent to prepare a polymer solution and dispersing this polymer solution in a non-aqueous solvent to form a W/O emulsion (Preparation Examples 1 to 5), the dynamic binding capacity became particularly large.

The invention claimed is:

1. A method for producing a porous particle, the method comprising:

(1) dissolving at least one polymer selected from the group consisting of a vinyl alcohol polymer and an ethylene-vinyl alcohol copolymer in an aqueous solvent to prepare a polymer solution;
(2) dispersing the polymer solution in a non-aqueous solvent to form a W/O emulsion;
(3) cooling the W/O emulsion to form a porous particle;
(4) chemically crosslinking the porous particle by reacting the porous particle with an aldehyde crosslinking agent to obtain a chemically crosslinked porous particle containing a formyl group;
(5) contacting the chemically crosslinked porous particle containing a formyl group with at least one polymer selected from the group consisting of a vinyl alcohol polymer and an ethylene-vinyl alcohol copolymer in the presence of an acid catalyst; and
(6) introducing a reactive functional group capable of binding to a ligand into the porous particle, wherein the reactive functional group is an epoxy compound;
wherein in step (5) the formyl group of the chemically crosslinked porous particle reacts with a hydroxyl group of the at least one polymer and chemically blocks the formyl group.

2. The method according to claim 1, wherein the at least one polymer comprises an ethylene-vinyl alcohol copolymer having a repeating unit derived from ethylene represented by Formula (1) in an amount exceeding 0% by mole and 50% by mole or less relative to an entire repeating unit in the ethylene-vinyl alcohol copolymer:

(1)

3. The method according to claim 1, wherein the aqueous solvent is a mixed solvent comprising:
at least one selected from the group consisting of a solvent miscible with water among sulfoxide-based solvents, a solvent miscible with water among polyol-based solvents, a solvent miscible with water among alcohol-based solvents, and a solvent miscible with water among amide-based solvents, and water; or
water.

4. The Method according to claim 1, wherein said contacting a chemically crosslinked porous particle in step (5) is with an ethylene-vinyl alcohol copolymer.

5. The method according to claim 1, wherein said contacting a chemically crosslinked porous particle in step (5) is with a vinyl alcohol copolymer.

6. The method according to claim 1, wherein the chemical crosslinking of step (4) is conducted in the presence of an acid catalyst.

7. The method according to claim 6, wherein the acid catalyst employed is the same acid catalyst present in the contacting of step (5).

8. The method according to claim 7, wherein the acid catalyst is sulfuric acid.

* * * * *